United States Patent [19]

Wright

[11] Patent Number: 4,540,786

[45] Date of Patent: Sep. 10, 1985

[54] PREPARATION OF 2-CHLORO-3-CYANO-QUINOLINES

[75] Inventor: Terry L. Wright, Clayton, Calif.

[73] Assignee: The Dow Chemical Company, Midland, Mich.

[21] Appl. No.: 524,970

[22] Filed: Aug. 22, 1983

[51] Int. Cl.³ .......................................... C07D 215/16
[52] U.S. Cl. .................................... 546/162; 546/114; 260/465 E; 260/465 B
[58] Field of Search ...................... 546/162; 260/465 B

[56] References Cited

PUBLICATIONS

Barnett et al., Can. J. Chem., vol. 58, pp. 409–411 (1980).
Meth–Cohn et al., "Tet. Letters", No. 23, pp. 2045–2048 (1978).
Meth–Cohn et al., "Tet. Letters", No. 33, pp. 3111–3114 (1978).
Meth–Cohn et al., Synthesis, Feb. 1980, pp. 133–135.
Meth–Cohn et al., J. Chem. Soc. *Perkin Trans*, pp. 1520–1543 (1981).
Ellingsfeld et al., Angew. Chem. 72, pp. 836–875 (1960).
J. March, Adv. Org. Chem., 2nd Ed., p. 827 (1977).
Dalcere, Tetrahedron Letters, vol. 22, No. 17, pp. 1599–1600 (1981).

*Primary Examiner*—Glennon H. Hollrah
*Assistant Examiner*—D. B. Springer
*Attorney, Agent, or Firm*—Michael L. Glenn

[57] ABSTRACT

A process is described for introducing nitrile groups to compounds susceptible to Vilsmeier formylation via two sequential reactions in a single reaction medium. In the first reaction, the susceptible compound is reacted with a Vilsmeier reagent in the presence of phosphorus oxychloride. In the second reaction, a hydroxylamine salt is introduced to the medium in the presence of at least an equivalent amount of phosphorus oxychloride.

8 Claims, No Drawings

PREPARATION OF 2-CHLORO-3-CYANO-QUINOLINES

BACKGROUND OF THE INVENTION

This invention relates to a process for introducing nitrile groups to compounds susceptible to Vilsmeier formylation. More specifically, a process is disclosed for introducing a nitrile group via two sequential reactions in a single reaction medium.

The formylation of aromatic and heterocyclic compounds by reaction with dialkylformamides or alkylarylformamides in the presence of phosphorus oxychloride is well known in the art. This reaction is commonly referred to as the Vilsmeier reaction.

It is also known that aldehydes can be converted to nitriles by reacting them with hydroxylamine hydrochloride in the presence of concentrated HCl or a dehydrating agent. J. March, *Advanced Organic Chemistry*, 2nd Ed., p. 827 (1977); Findlay et al, *Can. J. Chem.*, 45, 1014 (1967) and VanEs, *J. Chem. Soc.*, 1564 (1965). In general, this nucleophilic displacement reaction proceeds most readily in base.

There is no suggestion in the prior art that the conversion of an aldehyde to a nitrile using hydroxylamine hydrochloride would proceed readily in the presence of such a strong acidic dehydrating agent as phosphorus oxychloride. The skilled artisan would expect $POCl_3$ to react rapidly and possibly explosively with the oxime intermediate produced by reaction between the hydroxylamine and aldehyde. Also the reaction between the hydroxylamine and aldehyde would be predicted to be very slow under such acidic conditions. Other undesirable reactions between the hydroxylamine and $POCl_3$ might also be anticipated.

A convenient method of introducing nitrile groups to aromatic or heterocyclic compounds in a single reaction medium without isolation of intermediates would be desirable. The subject process is such a method.

SUMMARY OF THE INVENTION

The subject invention is a method of introducing a nitrile group to a compound susceptible to Vilsmeier formylation. This method consists essentially of two steps. In the first step, the compound susceptible to Vilsmeier formylation is reacted in a liquid medium with a Vilsmeier reagent in the presence of phosphorus oxychloride so as to introduce aldehyde or precursors of aldehyde moieties. In the second step, hydroxylamine or a strong acid salt thereof is introduced to the liquid medium which also contains at least an equivalent amount of phosphorus oxychloride, so as to convert a major portion of the iminium salt and aldehyde moieties present to nitrile groups.

DETAILED DESCRIPTION OF THE INVENTION

Formylation Reaction

The Vilsmeier reagents referred to herein are well-known compounds. Generally, they are reaction products of $POCl_3$ and disubstituted amides. These diamides generally correspond to the formula

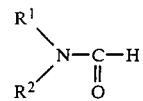

wherein $R^1$ is an alkyl group and $R^2$ is an alkyl or aryl group. Preferably $R^1$ is a $C_1$ to $C_4$ alkyl, most preferably methyl. Preferably $R^2$ is phenyl or a $C_1$ to $C_4$ alkyl, most preferably methyl or phenyl.

Compounds susceptible to Vilsmeier formylation are likewise well-known. These compounds are generally aromatic hydrocarbons or heterocycles which have an aromatic system more "electron rich" than benzene. Certain unsaturated aliphatic compounds bearing electron-donating substituents are also operable, e.g., 1,2-dimethoxyethane. Preferred heterocyclic compounds include thiophene or pyrrole, optionally substituted with one or more substituents. Preferred aromatic carbocyclic compounds include a benzene bearing at least one substituent having more electron donating character than hydrogen.

Some of these preferred reactants can be represented by the following formulae:

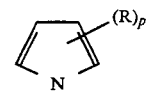   I

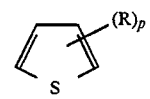   II

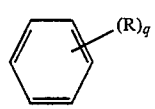   III wherein R at each occurrence is independently $-SC_nH_{2n+1}$, $-OC_nH_{2n+1}$, $-C_nH_{2n+1}$ or

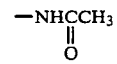

p is an integer from 0 to 3, q is an integer from 1 to 5, and n is an integer from 1 to 10, preferably 1. R can also be selected from $-Br$, $-Cl$, $-CN$, $-C_nH_{2n}CN$ or other electron withdrawing groups provided the compound remains more electron-rich than benzene. Preferably, p is an integer from 0 to 2, more preferably 0 or 1. Preferably q is 1 or 2.

In one preferred embodiment of the instant process the compound susceptible to Vilsmeier formylation corresponds to the formula

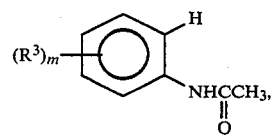

wherein $R^3$ is independently at each occurrence $-OC_nH_{2n+1}$, $-SC_nH_{2n+1}$ or $-C_nH_{2n+1}$, m is an integer from 0 to 4 and n is as described hereinbefore. This compound may bear one or more $-Cl$ or $-Br$ moieties, so long as there are sufficient electron donating substituents to make the aromatic ring more electron-rich than benzene.

The formylation of this compound in the presence of excess POCl₃ can produce in good yield a quinoline corresponding to the formula

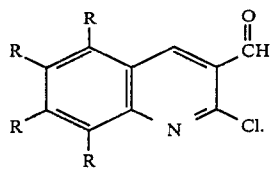

This reaction is described in some detail by Meth-Cohn et al in J. Chem. Soc., Perkin Trans. I, pp. 1520–1543 (1981).

The compound susceptible to Vilsmeier formylation and the Vilsmeier reagent are brought together at conditions known in the art to promote formylation. Conveniently, the Vilsmeier reagent and the susceptible compound are brought together in a stoichiometric ratio. A slight excess of the Vilsmeier reagent is preferred. The reactants are desirably combined slowly so as to avoid an excessive exotherm.

The temperature during the formylation is desirably maintained so that the desired reaction is not unduly slow. The reaction temperature should not be so high as to initiate an uncontrolled exothermic reaction or produce other deleterious effects. A reaction temperature in the range from about 70° to about 110° C. is generally preferred. Agitation of the medium to promote mass and heat transfer is advantageous.

The reaction medium desirably contains an excess of POCl₃ over that required to form the Vilsmeier reagent. An excess of at least 25 percent over the quantity of POCl₃ reacted with the diamide to form the Vilsmeier reagent is generally preferred. The POCl₃ can be employed in such excess as to be the major component in the reaction medium. However, generally it is preferred that the POCl₃ constitute no more than about 75 weight percent of the reaction medium.

The formylation reaction can be conducted in the presence of diluents inert in the reaction, such as 1,2-dichloroethane. However, recovery of the final product from the reaction medium is generally facilitated by conducting the reactions without inert diluents, i.e., neat.

The product of the formylation reaction is an iminium salt, i.e.,

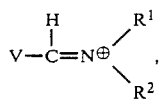

wherein "V" is derived from the compound susceptible to formylation and R¹ and R² are as defined hereinbefore. The iminium salt in the presence of water hydrolyzes spontaneously to an aldehyde and an amine. However, it is advantageous to conduct the instant reaction at anhydrous conditions. Consequently, the iminium salt is not generally hydrolyzed in the subject process.

Conversion to Nitrile

The product of the formylation reaction can be reacted with hydroxylamine or a strong acid salt thereof in the same reaction medium to convert the aldehyde or iminium salt moiety to a nitrile group. The formylation reaction product is not isolated. No additional POCl₃ need be added to the reaction mixture, if the excess POCl₃ stated to be advantageous was employed in the formylation reaction. Generally, it is desirable that the POCl₃ relative to the hydroxylamine be present in a molar ratio in the range from about 2:1 to about 6:1. An approximately stoichiometric amount or slight excess of NH₂OH relative to the aldehydes or aldehyde precursors present is desirable.

The hydroxylamine reactant is desirably used in the form of a salt of a strong mineral acid, e.g., HCl, H₂SO₄ or HBr. The hydrochloride salt of hydroxylamine is particularly preferred. Although the order in which the reactants are combined is not critical, preferably the hydroxylamine is added to the product of the formylation reaction at a rate which results in a controllable exotherm and gas evolving at a rate which avoids excessive foaming of the medium. An inert gas, such as nitrogen, can be blown over the medium to moderate foaming.

The temperature during conversion to the nitrile can generally be in the same range as employed during the formylation reaction. Temperatures in the range from about 60° to about 110° C. are preferred for reasons of convenience.

Recovery of Product

The product bearing the nitrile group can be readily recovered by conventional methods known in the art. Typically, sufficient water is added to the reaction mixture to react with any remaining POCl₃ before attempting to recover the product.

The desired product often precipitates from the reaction mixture and can be recovered by filtration. The precipitate can be recrystallized in CH₂Cl₂ or other similar organic solvents to increase purity.

Alternatively, the reaction medium after quenching with H₂O can be contacted with an organic solvent such as CH₂Cl₂ to extract the product. The organic solvent can then be separated and evaporated from the product.

Other methods for recovering the desired product are known in the art. The subject invention is not limited to any specific method for recovery of this product.

The resulting products are useful as intermediates for a variety of pharmaceutical or other compositions. See, e.g., U.S. patent application Ser. No. 478,964, filed Mar. 25, 1983, U.S. Pat. No. 4,496,569 issued 11/29/85.

The following examples are presented to illustrate the invention but are not otherwise intended to limit the invention.

EXAMPLE 1

To a reaction vessel containing 25 grams (0.18 mole) of acetanilide were added concurrently 41 grams (0.54 mole) of dimethylformamide (DMF) and 118 milliliters (1.26 moles) of POCl₃ over a period of 15 minutes. During addition the reaction mixture was stirred, purged with nitrogen gas and maintained at a temperature of 60° to 75° C. After addition, the stirred mixture was maintained at 75° C. for 20 hours.

The mixture was allowed to cool to 62° C. and then 14 grams (0.2 mole) of NH₂OH HCl was added all at one time to the stirred mixture. (Slower addition of NH₂OH HCl is recommended when larger quantities are involved.) Gas evolution was observed after about 2 minutes. The temperature of the reaction medium increased due to the exothermic reaction to 77° C. over a period of 15 minutes. The mixture was allowed to cool to ambient temperature (about 20° C.). A yellow, dense, solid precipitate was observed.

To the resulting mixture was added with vigorous stirring 100 milliliters (ml) of distilled water. The mixture was filtered to recover 24.3 grams (g) of a yellow solid having a melting point of 145°–160° C. This crude product was recrystallized in CH₂Cl₂ to recover 15.5 grams of light yellow crystals having a melting point of 165° C. The product was identified by infrared spectroscopy, proton magnetic resonance analysis and other conventional techniques to correspond to the formula

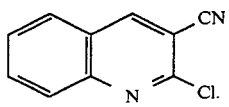

The isolated yield of this product was 44%.

EXAMPLE 2

In a manner and mole ratios otherwise generally similar to Example 1, dimethylaniline (instead of acetanilide) was reacted with dimethylformamide and POCl₃ for two hours at reflux. The mixture was cooled to 70° C. and hydroxylamine.HCl was added. The exothermic reaction raised the temperature of the medium to 90° C.

Water was added to the reaction mixture after the reaction appeared complete. The mixture was extracted with CH₂Cl₂. The CH₂Cl₂ was separated and then evaporated to yield a dark brown oil. This oil was determined by conventional analytical techniques to consist predominantly of dimethylaminobenzonitrile,

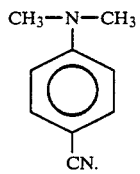

EXAMPLE 3

3,4-Dimethoxyacetanilide (25 g, 0.13 mole) was added to a 300 ml round-bottom flask containing phosphoryl chloride (119 ml, 1.3 mole). DMF (24 g, 0.32 mole) was added dropwise to the stirred solution at a rate such that the temperature of the reaction mixture remained below 80°–90° C. After the addition was complete, the reaction mixture was heated to reflux (~105° C.) for 2.5 hours.

Hydroxylamine.HCl (13.3 g, 0.19 mole) was added to the reaction mixture in small portions over a period of about 20 minutes. Vigorous foaming (HCl evolution) occurred a few seconds after addition of each portion of NH₂OH HCl, and sufficient time for the foam layer to form and subside was allowed between portions.

After addition of hydroxylamine was complete, the mixture was heated to reflux for an additional 10–15 minutes, and the hot reaction mixture was quenched in water (~600 ml). The mixture was filtered, yielding 21.8 g of a brown solid. The solid was analyzed via proton magnetic resonance analysis and confirmed to correspond to predominantly 2-chloro-6,7-dimethyoxy-3-quinolinecarbonitrile. The crude product was dissolved in 300 ml of hot chloroform, treated with charcoal and filtered. The filtrate was combined with ethanol and the resulting solution refluxed until crystallization was observed. The solution was cooled and filtered to recover 15.7 g of light yellow product.

EXAMPLE 4

4-Methylthioacetanilide (63 g, 0.35 mole) was added to a reaction flask containing phosphoryl chloride (2.24 ml, 2.45 mole). Dimethylformamide (77 g, 1.05 mole) was added dropwise to the stirred solution at a rate such that the temperature of the reaction mixture remained below 75° C. After the addition was completed, the reaction mixture was heated to 75° C. for 16 hours.

Hydroxylamine hydrochloride (34.7 g, 0.5 mole) was added to the reaction mixture in small portions over a period of about 15 minutes. The temperature of the reaction mixture rose to 95° C. over the course of addition. After an additional 15 minutes at 95° C., the reaction was quenched with water (1500 ml). The resulting precipitate was collected and dried to recover 42.7 g (52% yield) of crude product. The product was analyzed by conventional methods and determined to correspond to the formula:

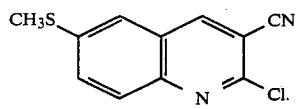

A sample was recrystallized from methylene chloride/hexane to yield yellow needles melting at 227°–228° C.

EXAMPLE 5

N-(thien-3-yl)-acetamide (3.0 g, 0.02 mole) was added to a solution of phosphoryl chloride (23 g, 0.15 mole) and dimethylformamide (4.3 g, 0.059 mole) at ambient temperatures. The resulting solution was heated to reflux for 1.5 hours, and then NH₂OH HCl (2 g, 0.03 mole) was added slowly over a period of 10 minutes. After the reaction subsided, the mixture was cooled to 25° C. and filtered. The collected solid was washed with water and dried to yield 2.1 g (51%) of product. The light yellow solid melted at 222°–224° C.

The product was confirmed by conventional analytical methods to correspond to the formula:

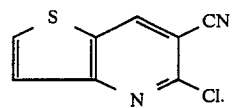

EXAMPLE 6

A stirred mixture of 3-thienylacetonitrile (25 g, 0.21 mole), phosphoryl chloride (135 ml, 1.47 mole), and DMF (46 g, 0.63 mole) was heated to reflux for 2.5 hours. Hydroxylamine hydrochloride (29.2 g, 0.4 mole) was added in portions over a period of 20 minutes. After the addition was complete, the mixture was cooled and filtered to yield 26 g of product as a yellow solid. A sample was recrystallized from acetone to give fluffy white needles, m.p. 208°–209° C.

The product was confirmed by conventional analytical methods to correspond to the formula:

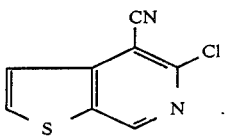

What is claimed is:

1. A method of introducing a nitrile group to a compound susceptible to Vilsmeier formylation corresponding to the formula

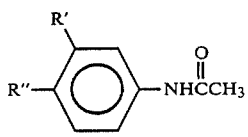

wherein R' is —H, $C_1$-$C_4$ alkoxy, —Cl, —Br or $C_1$-$C_4$ alkyl and R" is —H, $C_1$-$C_4$ alkoxy, —Cl, —Br, $C_1$-$C_4$ alkyl or —$SCH_3$, comprising the steps of:
 (a) reacting the compound susceptible to Vilsmeier formylation in a liquid medium with a Vilsmeier reagent in the presence of excess phosphorus oxychloride;
 (b) to the same reaction medium in the presence of phosphorus oxychloride introduce hydroxylamine or a protic acid salt thereof so as to introduce nitrile groups to a major portion of the compounds that reacted with the Vilsmeier reagent, so as to prepare a compound of the formula

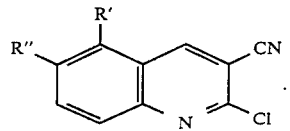

2. The method as described in claim 1 wherein the compound susceptible to Vilsmeier formylation is brought together with at least a stoichiometric amount of a Vilsmeier reagent.

3. The method as described in claim 2 wherein the liquid reaction medium is essentially anhydrous.

4. The method as described in claim 3 wherein in step (a) $POCl_3$ is present in at least 25 percent excess over that required to convert a disubstituted amide to the Vilsmeier reagent present in the medium.

5. The method as described in claim 4 wherein in step (b) the molar ratio of hydroxylamine to $POCl_3$ is in the range from about 1:2 to about 1:6.

6. The method as described in claim 5 wherein the hydroxylamine is present in the form of a hydrochloride salt.

7. The method as described in claim 6 wherein in step (a) the reaction temperature is in the range from about 70° to about 110° C.

8. The method as described in claim 7 wherein in step (b) the reaction temperature is in the range from about 60° to about 110° C.

* * * * *